United States Patent
Buccafusca (10) Patent No.: US 9,103,764 B2
(45) Date of Patent: Aug. 11, 2015

(54) METHOD AND SYSTEM FOR DETERMINING THE TIME-OF-FLIGHT OF AN ACOUSTIC SIGNAL

(75) Inventor: Osvaldo Buccafusca, Fort Collins, CO (US)

(73) Assignee: Avago Technologies General IP (Singapore) Pte. Ltd., Singapore (SG)

(*) Notice: Subject to any disclaimer, the term of this patent is extended or adjusted under 35 U.S.C. 154(b) by 383 days.

(21) Appl. No.: 12/782,117

(22) Filed: May 18, 2010

(65) Prior Publication Data

US 2011/0288795 A1 Nov. 24, 2011

(51) Int. Cl.

| | |
|---|---|
| *G01N 29/07* | (2006.01) |
| *G01F 23/296* | (2006.01) |
| *G01N 29/38* | (2006.01) |
| *G01F 23/284* | (2006.01) |
| *G01N 29/44* | (2006.01) |
| *G01S 11/16* | (2006.01) |

(52) U.S. Cl.
CPC .......... *G01N 29/07* (2013.01); *G01F 23/2962* (2013.01); *G01N 29/38* (2013.01); *G01F 23/284* (2013.01); *G01N 29/4454* (2013.01); *G01S 11/16* (2013.01)

(58) Field of Classification Search
USPC .............. 702/38, 39, 48, 56, 79, 89, 103, 159, 702/171
See application file for complete search history.

(56) References Cited

U.S. PATENT DOCUMENTS

| | | | |
|---|---|---|---|
| 5,517,994 A | 5/1996 | Burke et al. | |
| 5,818,735 A | 10/1998 | Tigwell et al. | |
| 5,920,278 A | 7/1999 | Tyler et al. | |
| 5,983,730 A | 11/1999 | Freund et al. | |
| 6,131,076 A | 10/2000 | Stephan et al. | |
| 6,504,793 B2 | 1/2003 | Fuenfgeld | |
| 6,865,137 B2 | 3/2005 | Lyon et al. | |
| 7,010,973 B2 | 3/2006 | Bartoli et al. | |
| 7,010,974 B2 | 3/2006 | Spanke et al. | |
| 7,334,451 B1* | 2/2008 | Fauveau | 73/1.73 |
| 2005/0172707 A1* | 8/2005 | Kanatani et al. | 73/146 |
| 2006/0239121 A1* | 10/2006 | Kong et al. | 367/128 |
| 2007/0051486 A1* | 3/2007 | IIzuka et al. | 164/454 |
| 2008/0024145 A1 | 1/2008 | Schultheiss et al. | |
| 2008/0204223 A1* | 8/2008 | Chu et al. | 340/539.13 |
| 2010/0005890 A1* | 1/2010 | Miyamoto | 73/597 |
| 2011/0303014 A1* | 12/2011 | Kajitani | 73/632 |
| 2012/0044786 A1* | 2/2012 | Booij et al. | 367/127 |

OTHER PUBLICATIONS

J. Edwards, "Frequency Domain Theory and Applications", DSP Numerix, 2006, pp. 1-42.
V. Toronov et al., "Optimization of the Signal-to-Noise Ratio of Frequency-Domain Instrumentation for Near-Infrared Spectro-Imaging of the Human Brain", Optics Express, vol. 11, No. 21, Oct. 20, 2003, pp. 2717-2729.

* cited by examiner

*Primary Examiner* — Sujoy Kundu
*Assistant Examiner* — Paul D Lee (57) ABSTRACT

A method of estimating the time and flight of an acoustic signal transmitted by a transmit acoustic transducer determines a difference in time between receiving the transmitted acoustic signal and receiving an electromagnetic wave transmitted by the transmit acoustic transducer coincident with transmitting the acoustic signal.

20 Claims, 6 Drawing Sheets

METHOD AND SYSTEM FOR DETERMINING THE TIME-OF-FLIGHT OF AN ACOUSTIC SIGNAL

BACKGROUND

Figure 1:
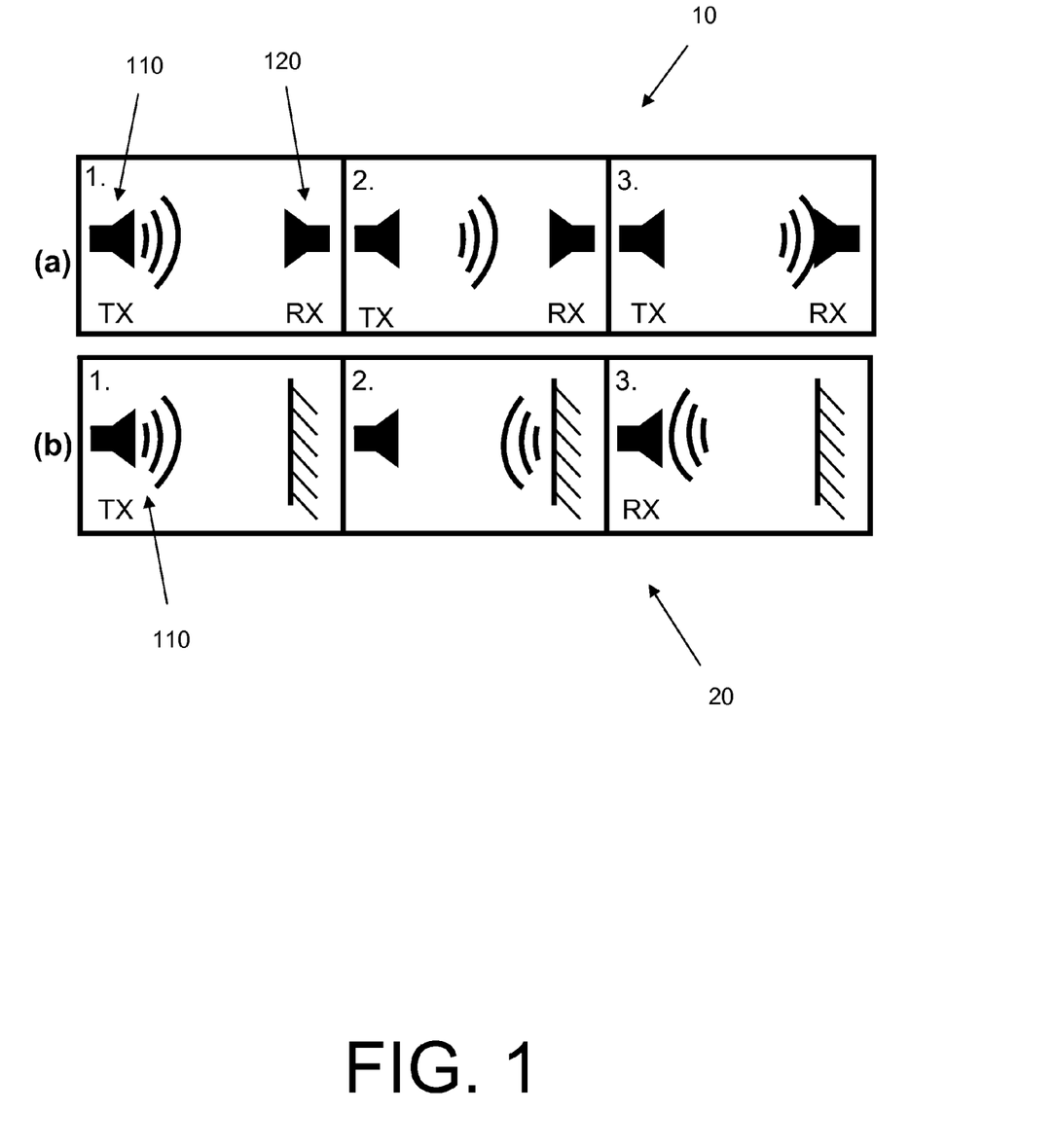
FIG. 1A illustrates an example of a time-of-flight (TOF) measurement system with a pitch-catch configuration.
FIG. 1B illustrates an example of a time-of-flight (TOF) measurement system with a pulse-echo configuration.

There are a number of applications where determining the time-of-flight (TOF) of an acoustic signal is required. These applications include ultrasonic level detectors and ultrasonic flow meters. In general, a system for determining TOF of an acoustic signal can take two forms: pitch-catch and pulse-echo. FIG. 1A illustrates an example of a pitch-catch TOF measurement system, and FIG. 1B shows an example of a pulse-echo TOF measurement system. In either configuration, a device 110 (e.g., an acoustic transducer) transmits an acoustic signal at a predetermined time and the acoustic signal is then sensed some time later. In a pitch-catch system shown in FIG. 1A, the acoustic signal is sensed by a second, separate, receive (RX) device 120 (e.g., another acoustic transducer). In the pulse-echo system shown in FIG. 1B, the acoustic signal is sensed with the same device 110 that transmitted the signal—i.e., the device 110 is both the TX device and the RX device. The time it takes the signal to traverse from the TX device to the RX device is the time-of-flight of the signal.

Achieving a required degree of accuracy in the time-of-flight measurement of an acoustic signal is both critical and difficult.

For one thing, to measure the time-of-flight of the acoustic signal the RX device requires accurate information identifying the time when the acoustic signal was transmitted by the TX device. This presents limitations, particularly in the case of a pitch-catch system. If a copy of the electrical signal driving the acoustic transducer in the TX device is used for the receive device's reference, then some means must be provided to communicate a sample of that electrical signal from the TX device to the RX device. Furthermore, a sample the electrical signal driving the acoustic transducer in the TX device does not reflect the delay in the acoustic transducer.

What is needed, therefore, is an accurate method of estimating the time-of-flight of an acoustic (e.g., an ultrasound) signal. What is also needed is a system which can accurately estimate the time-of-flight of an acoustic signal.

SUMMARY

In an example embodiment, a method comprises: providing a drive electrical signal to a transmit acoustic transducer in a transmit device; in response to the drive electrical signal, transmitting both an electromagnetic wave and an acoustic signal from the transmit acoustic transducer; receiving the electromagnetic wave at a receive acoustic transducer of a receive device; detecting a first feature of the received electromagnetic wave and determining a first time corresponding to the first feature; receiving the acoustic signal at the receive acoustic transducer of the receive device; detecting a second feature of the received acoustic signal and determining a second time corresponding to the second feature; determining a difference between the second time and the first time; and estimating the time-of-flight of the acoustic signal as the difference between the second time and the first time.

In another example embodiment, an apparatus comprises: a receive device including a receive acoustic transducer; and a processor configured to cause the receive device to execute an algorithm. The algorithm comprises: receiving at the receive acoustic transducer an electromagnetic wave that is emitted by a transmit acoustic transducer coincident with transmitting an acoustic signal; detecting a first feature of the received electromagnetic wave and determining a first time corresponding to the first feature; receiving the acoustic signal at the receive acoustic transducer; detecting a second feature of the received acoustic signal and determining a second time corresponding to the second feature; determining a difference between the second time and the first time; and estimating the time-of-flight of the acoustic signal as the difference between the second time and the first time.

In yet another embodiment, a method is provided for estimating the time-of-flight of an acoustic signal transmitted by a transmit acoustic transducer. The method comprises determining a difference in time between receiving the transmitted acoustic signal and receiving an electromagnetic wave transmitted by the transmit acoustic transducer coincident with transmitting the acoustic signal.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions shown in the drawings may be arbitrarily increased or decreased for clarity of discussion. Wherever applicable and practical, like reference numerals refer to like elements.

DETAILED DESCRIPTION

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparati and methods may be omitted so as to not obscure the description of the example embodiments. Such methods and apparati are clearly within the scope of the present teachings.

Unless otherwise noted, when a first device is said to be connected to a second device, this encompasses cases where one or more intermediate devices may be employed to connect the two devices to each other. However, when a first device is said to be directly connected to a second device, this encompasses only cases where the two devices are connected to each other without any intermediate or intervening devices. Similarly, when a signal is said to be coupled to a device, this encompasses cases where one or more intermediate devices may be employed to couple the signal to the device. However, when a signal is said to be directly coupled to a device, this encompasses only cases where the signal is directly coupled to the device without any intermediate or intervening devices.

The inventor has appreciated that in addition to acoustic signals, piezoelectric bulk and microelectromechanical system (MEMS) acoustic transducers emit and receive electromagnetic radiation due to their impedance characteristics. More specifically, when a piezoelectric bulk or MEMS acoustic transducer (e.g., an ultrasonic transducer) is excited with an electrical signal such as an AC burst with a frequency equal to the transducer's resonance frequency, the transducer emits an acoustic signal (e.g. an acoustic pulse), but at the same time it also transmits part of the electrical signal used to drive it in the form of a electromagnetic wave (e.g., an electromagnetic pulse). Furthermore, when a receive acoustic transducer receives the electromagnetic wave, it will produce an output signal in response to the received electromagnetic wave, and when it receives the acoustic signal, it will provide an output signal in response to the received acoustic signal.

Figure 2:
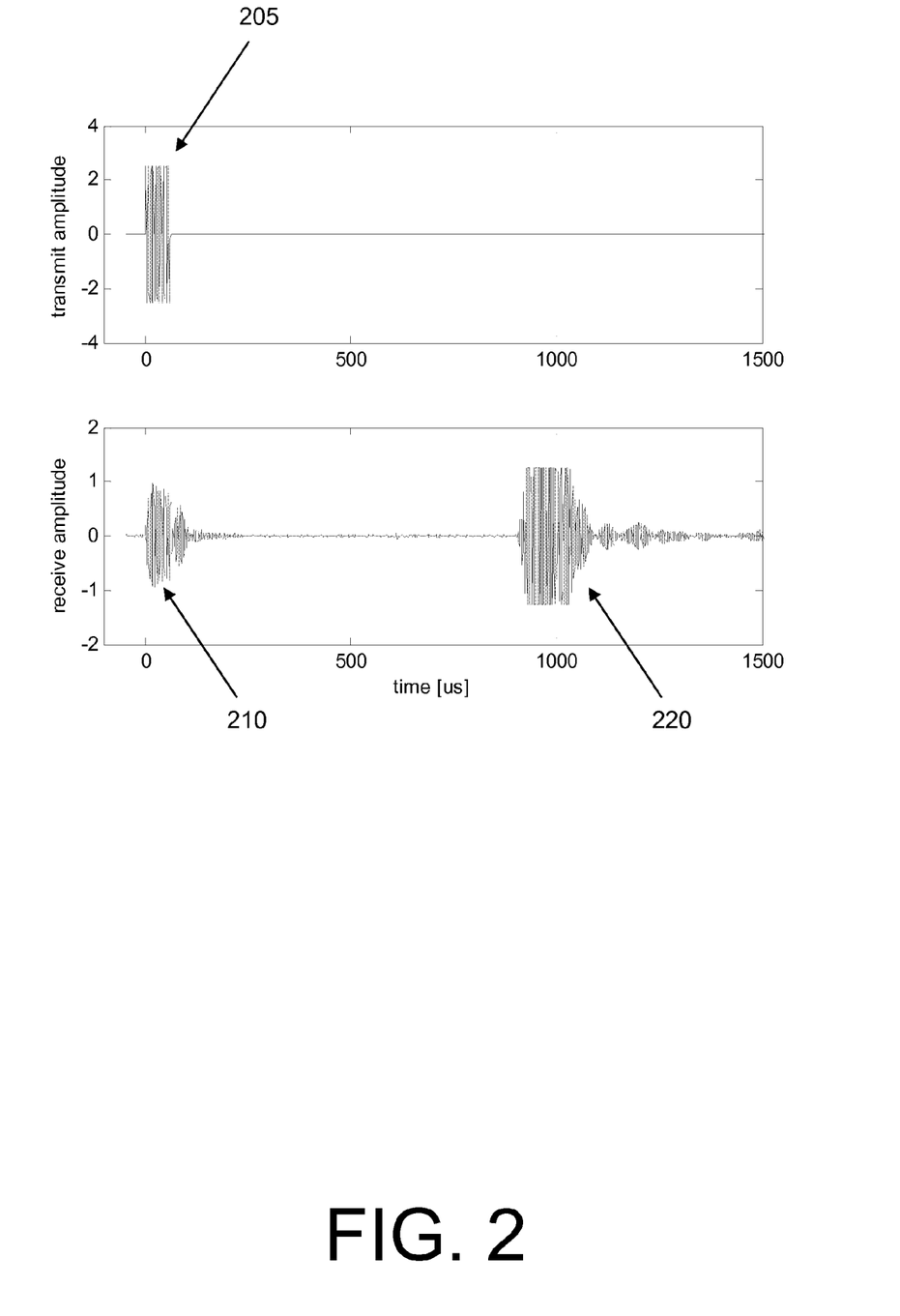
FIG. 2 illustrates transmit and received signals in a pitch-catch TOF measurement system.

FIG. 2 illustrates transmitted and received signals in a pitch-catch time-of-flight (TOF) measurement system that employs transmit and receive acoustic transducers. The top trace in FIG. 2 illustrates the signal 205 transmitted by the transmit acoustic transducer, and the bottom trace illustrates the signals received by the receive acoustic transducer. As shown in the bottom trace, the receive acoustic transducer first receives the electromagnetic wave 210 that was transmitted by the transmit acoustic transducer coincident with the acoustic signal. Then at a subsequent time, the receive acoustic transducer receives the acoustic signal 220 that was transmitted by the transmit acoustic transducer.

In the past, this electromagnetic radiation has usually been considered a source of noise in the receiver that needs to be eliminated when attempting to measure the time-of-flight $t_{TOF}$ of an acoustic signal.

However, the inventor has appreciated that this electromagnetic wave can be used to determine the time-of-flight reference time (i.e., the time when the acoustic signal was transmitted) in a TOF measurement system.

The electromagnetic pulse travels at the speed of light, while the acoustic pulse travels at the much slower speed of sound. If a receive transducer receives both the electromagnetic wave and the acoustic signal, then the time-of-flight $t_{TOF}$ of the acoustic signal can be estimated by using the electromagnetic wave for generating a timing reference $t_{REF}$ representing the estimated time when the acoustic signal was transmitted.

Figure 3:
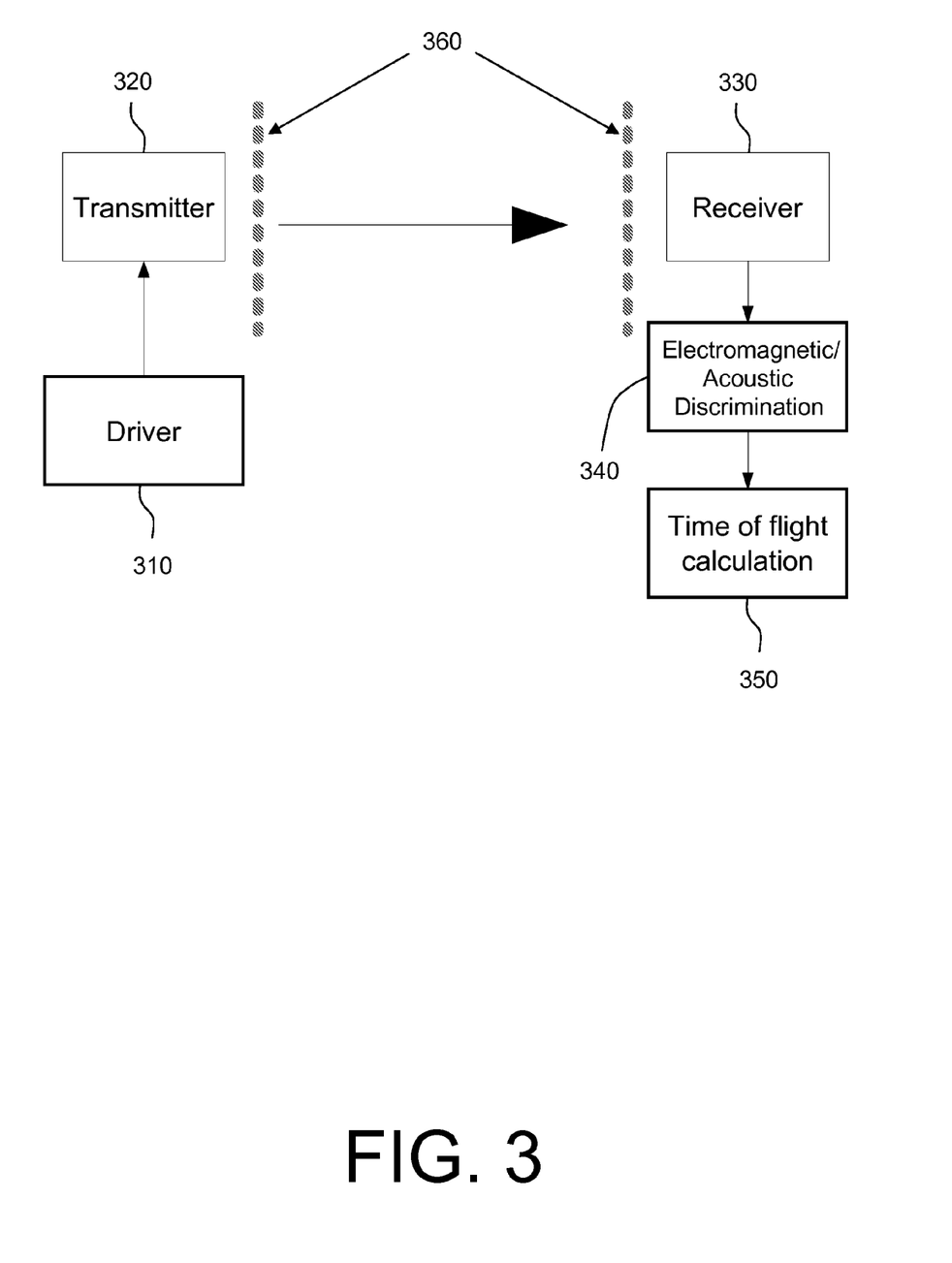
FIG. 3 is a functional drawing illustrating some operations of one embodiment of a system for measuring the TOF of an acoustic signal.

FIG. 3 is a functional drawing illustrating some operations of one embodiment of a system for measuring the time-of-flight $t_{TOF}$ of an acoustic signal. As shown in FIG. 3, a driver 310 applies a drive electrical signal to a transmitter 320 including a transmit acoustic transducer. The drive electrical signal may have any one or a number of different forms, including a pulsed sinusoid, a series of pulses, etc. The drive electrical signal may be amplitude, phase and/or frequency modulated. Driver 310 may generate the drive electrical signal under control of a processor or controller not shown in the functional drawing of FIG.

In response to the drive electrical signal, transmitter 320 transmits an acoustic signal. Coincident with the acoustic signal, transmitter 320 also transmits an electromagnetic wave. The electromagnetic wave and the acoustic signal are received by a receiver 330, including a receive acoustic transducer. The received signal is amplified and conditioned appropriately and then in block 340 the electromagnetic signal is discriminated from the acoustic signal. This can be achieved using the properties of the signals themselves, or by the use of appropriate time windows. In block 350 the time-of-flight $t_{TOF}$ is then estimated as the difference between time $t_{REC}$ when the received acoustic signal is received, and a time $t_{REF}$ when the electromagnetic wave is received, using any known time-domain or frequency domain time-of-flight measurement technique, examples of which will be described in greater detail below.

The embodiment shown in FIG. 3 includes selective electromagnetic shielding elements 360 at both transmit and receive devices 320 and 330 to allow a desired amount of the electromagnetic emission to be detected without affecting proper reception and detection of the acoustic signal. However, in some embodiments, either or both of the shielding elements 360 may be omitted—particularly in cases where the transducer construction and/or the operating environment provide the necessary ratio between the electromagnetic and acoustic emissions.

Figure 4:
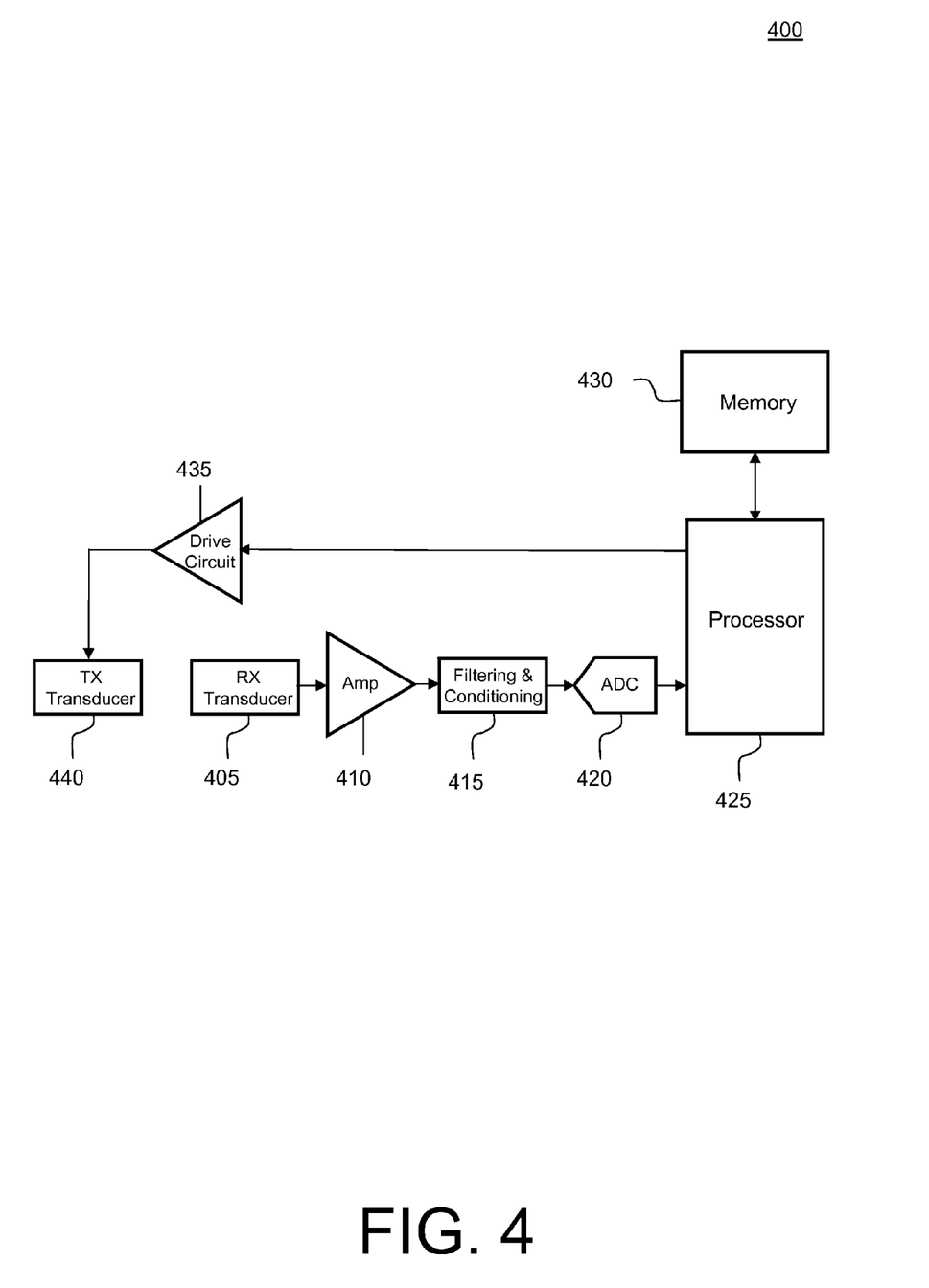
FIG. 4 shows a block diagram of one embodiment of a system for measuring the TOF of an acoustic signal.

FIG. 4 illustrates on embodiment of a system 400 for measuring the time-of-flight $t_{TOF}$ of an acoustic signal. System 400 includes a receive transducer 405, an optional amplifier 410, an optional filtering and conditioning stage 415, an analog-to-digital converter (ADC) 420, a processor 425, a memory 430, a drive circuit 435, and a transmit transducer 440.

In some embodiments, receive transducer 405 and transmit transducer 440 are each acoustic transducers—for example, ultrasonic transducers. In some embodiments, receive transducer 405 and transmit transducer 440 comprise piezoelectric bulk transducers or microelectromechanical system (MEMS) acoustic transducers.

Processor 425 may be a general purpose digital signal processor (DSP), microcontroller, programmable logic device, programmable gate array, custom ASIC, or a general purpose microprocessor executing a computer program, the executable code for which may be stored, for example, in memory 430. Beneficially, processor 425 generates either a digital transmit signal or an analog transmit signal via an on-board digital-to-analog converter (DAC). This signal may be routed to drive circuit 435, which amplifies the signal or otherwise converts it for application to transmit transducer 440. The received signal from receive transducer 405 may be amplified by amplifier 410, and then (optionally) is filtered by filtering and conditioning stage 415 and then sampled with analog-to-digital converter (ADC) 420. In an alternative embodiment, the analog-to-digital-conversion function may be performed with processor 425. The drive electrical signal provided from drive circuit 435 to transmit transducer 440 causes transmit transducer 440 to emit an acoustic signal, and at the same time transmit transducer 440 emits a corresponding electromagnetic wave.

Receive transducer 405 receives the electromagnetic wave and the acoustic signal. The received signals may be amplified by amplifier 410, and then may be filtered and conditioned by optional filtering and conditioning stage 415. ADC 420 converts the processed receive signal from an analog form to a digital form, and provides its digital output for further processing by processor 425.

Processor 425 may operate in conjunction with instructions in memory 430 to cause system 400 to execute a time-of-flight measurement algorithm, for example an algorithm 600 shown in FIG. 6 and described in detail below.

Figure 5:
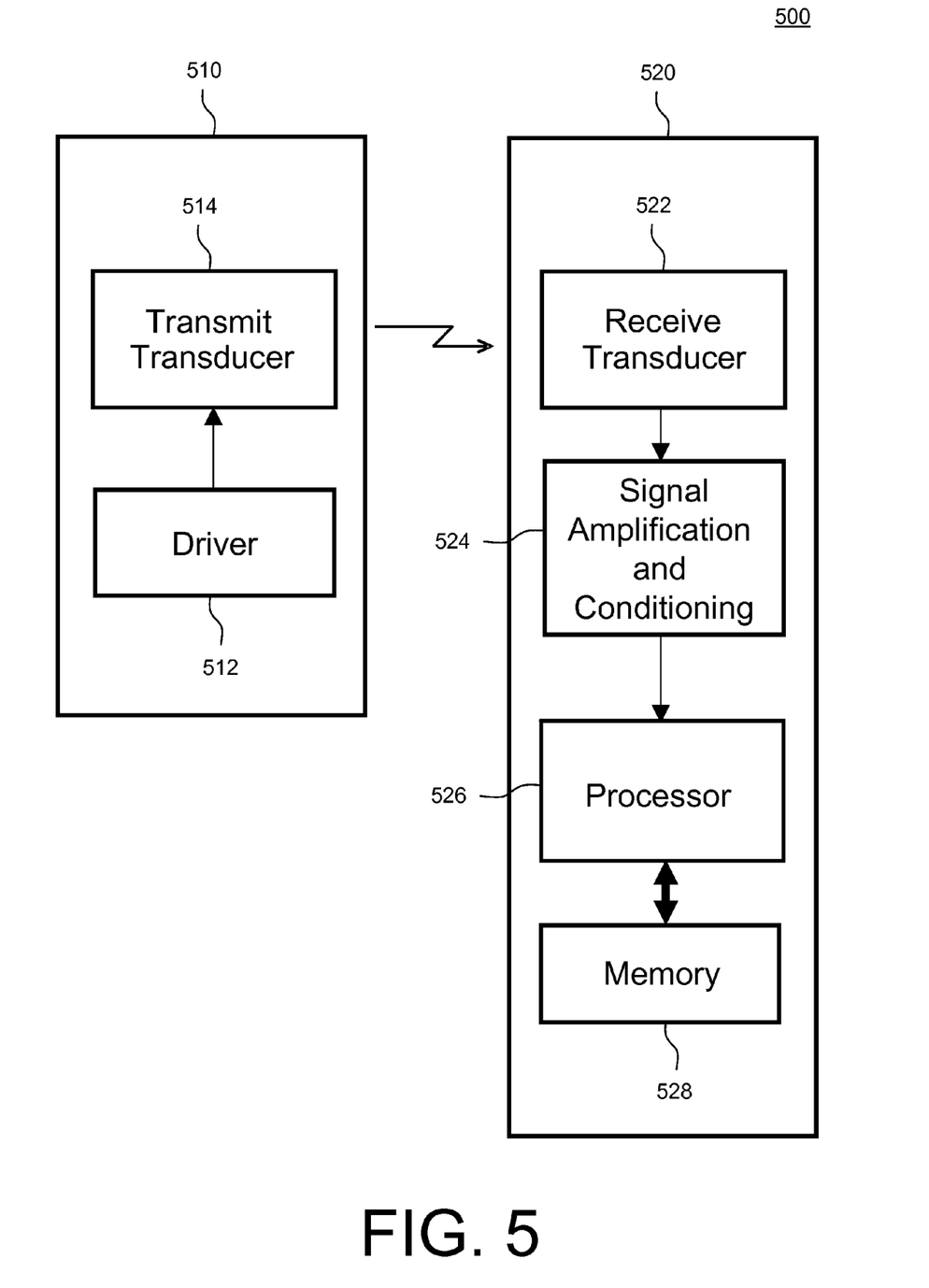
FIG. 5 shows a block diagram of another embodiment of a system for measuring the TOF of an acoustic signal.

FIG. 5 shows a block diagram of another embodiment of a system 500 for measuring the time-of-flight $t_{TOF}$ of an acoustic signal. TOF measurement system 500 includes a transmit subsystem 510 and a receive subsystem 520. Transmit subsystem 510 includes a driver 512 and a transmit acoustic transducer 514. In some embodiments, transmit subsystem 510 may include other components such as a processor, memory, etc. Receive device 510 includes a receive acoustic transducer 522, a signal amplification and conditioning stage 524, a processor 526, and memory 528. In some embodiments, signal amplification and conditioning stage 524 may include one or more amplifiers, filters, and an ADC. Processor 526 may be a general purpose digital signal processor (DSP), microcontroller, programmable logic device, programmable gate array, custom ASIC, or a general purpose microprocessor executing a computer program, the executable code for which may be stored, for example, in memory 528. Processor 526 may operate in conjunction with instructions stored in memory 528 to cause system 500 to execute a time-of-flight measurement algorithm, for example an algorithm 600 shown in FIG. 6 and described in detail below.

One difference between system 500 and system 400 is that in system 400 a processor 425 is in communication with both the transmit device and receive device, while in system 500 the processor 526 in receive subsystem 520 is not in communication with transmit subsystem 510. So in system 400 the processor 425 which executes an algorithm to estimate the TOF of the acoustic signal may have timing information pertaining to the drive electrical signal provided to drive circuit 435. In contrast in system 500, processor 526 may not know the time when driver 512 provides the electrical signal to drive transmit acoustic transducer 514. System 500 hence provides a significant simplified arrangement in situations where the transmit and receive transducers are located far apart.

As described above, a transmit device in a TOF measurement system transmits an electromagnetic wave coincident with transmitting an acoustic signal, and a receive device estimates the time-of-flight $t_{TOF}$ of the acoustic signal based on a time difference between when a time $t_{REC}$ when the acoustic signal is received, and a time $t_{REF}$ when the electromagnetic wave is received. In that case, the receive subsystem 520 applies some predetermined processing for determining the time $t_{REC}$ when the acoustic signal is received and for determining the time $t_{REF}$ when the electromagnetic wave is received.

In some embodiments, the receive device detects when the electromagnetic wave is received by detecting a first feature of the received electromagnetic wave and designating a first time corresponding to that first feature as the reference time $t_{REF}$. In that case, the reference time $t_{REF}$ may be a close approximation of the actual transmit time, with the "error" being the extremely small time delay of the propagation of the electromagnetic wave at the speed of light. The receive device detects when the acoustic signal is received by detecting a second feature of the received electromagnetic wave and designating a second time corresponding to that second feature as the time $t_{REC}$ when the acoustic signal was received. The receive device can then estimate the time-of-flight $t_{TOF}$ of the acoustic signal as the difference between the second time and the first time, namely:

$$t_{TOF} = t_{REC} - t_{REF} \quad (1)$$

In a beneficial arrangement, the first feature and the second feature correspond to each other, e.g., the first and second features were generated at the same time at the transmit acoustic transducer.

For example, in one embodiment the first feature may be an amplitude peak in the received electromagnetic wave and the second feature may be an amplitude peak in the received acoustic signal.

In another embodiment, a simple amplitude threshold technique might be employed. That is, the first feature may be a point where the received electromagnetic wave exceeds a first threshold, and the second feature may be a point where the received acoustic signal exceeds a second threshold.

However, in many systems an amplitude peak or an amplitude threshold will provide a less than desirable resolution. For example, when a system employs ultrasonic transducers, these transducers are resonant devices with a limited bandwidth, and therefore the signal has an associated envelope with a rise and fall time. Any additive noise in the system could cause false readings by either accelerating or decelerating the threshold crossing. In other cases, the signal may be attenuated in such a way that the threshold level is not crossed until the next oscillation cycle: This is commonly referred to as cycle slip.

A number of techniques have been used to improve the resolution of the TOF measurement. Some techniques employ correlation methods to detect timing features of the received electromagnetic wave and the received acoustic signal (e.g., the times when these signals each produce a correlation peak when correlated against some reference signal). Some techniques employ amplitude, phase or frequency modulation of the drive electrical signal, for example to place a "marker" in the transmitted signal, and corresponding demodulation of the received signal for example to detect the time when the marker was received.

For example, in one embodiment that uses a correlation technique, the receive subsystem may have (e.g., stored in memory, or provided from the transmit subsystem) a copy of the drive electrical signal which is employed to drive the transmit acoustic transducer, and may include a correlator that correlates the received electromagnetic wave with the copy of the drive electrical signal. In that case, the receive device may detect a correlation peak between the received electromagnetic wave and the copy of the drive electrical signal, and may designate the time when this correlation peak occurs as the reference time, $t_{REF}$. Similarly, the receive subsystem may detect a correlation peak between the received acoustic signal and the copy of the drive electrical signal, and may designate the time when this correlation peak occurs as the time when the acoustic signal is received, $t_{REC}$. Other embodiments of correlation techniques may be employed, including for example correlation between two received signals.

However, correlation techniques still rely heavily on the amplitude information in the signal, and correlation results can be corrupted by noise in the signal. Accordingly, in some embodiments, a modulation technique such as Frequency-Shift Keying (FSK), Phase-Shift Keying (PSK), Quadrature Modulation or Frequency Hopping is employed to provide the electrical drive signal driving the transmit transducer with a "marker" that can be used to define timing for the transmit signal. The receive subsystem demodulates the received electromagnetic signal and the received acoustic signal to identify the corresponding times when the marker is detected in the received electromagnetic signal and in the received acoustic signal, and designates these times as the reference time $t_{REF}$ and the signal reception time $t_{REC}$, respectively.

In some embodiments, the sampled receive data may require further manipulation or processing before the TOF measurement methods described above may be performed.

Figure 6:
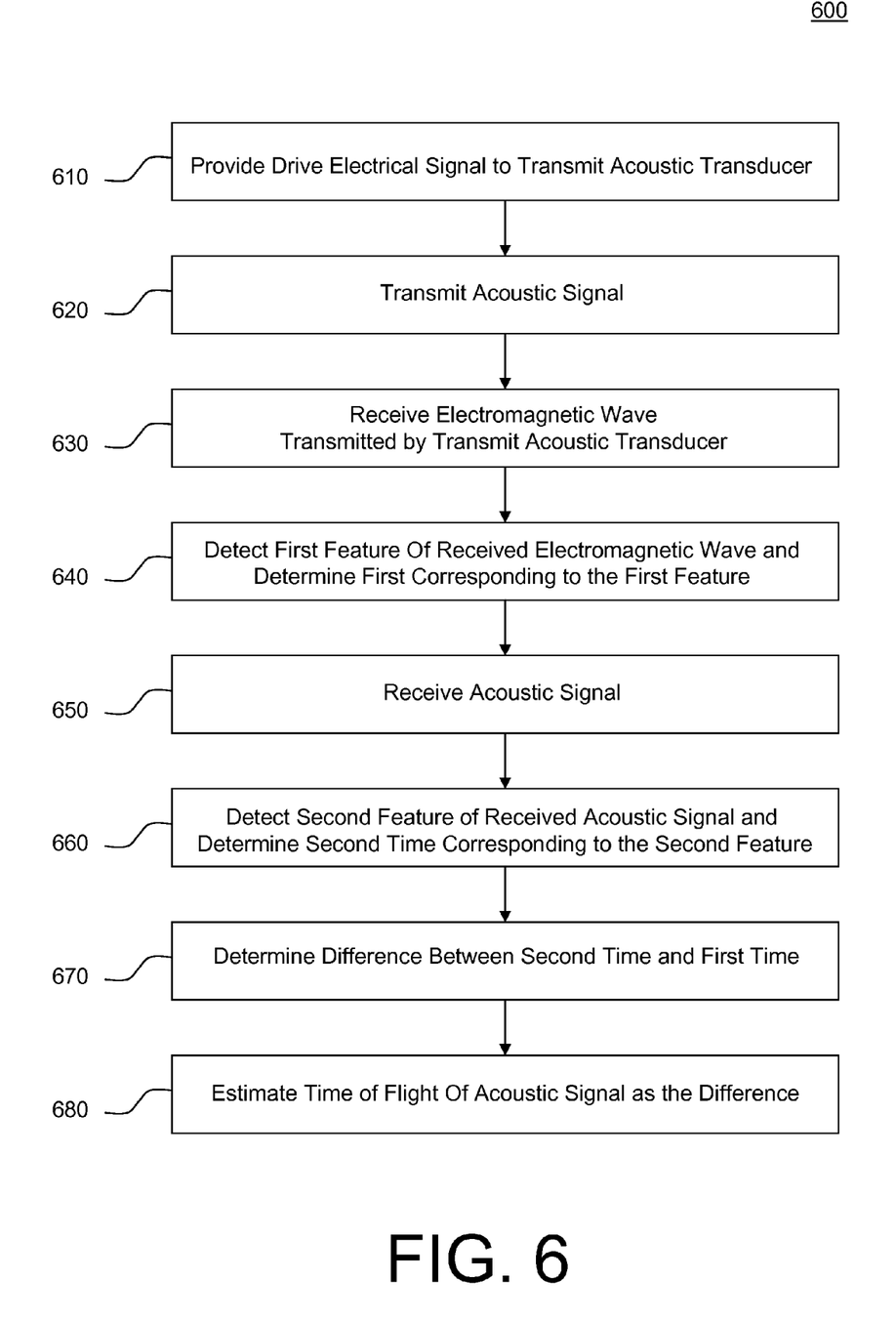
FIG. 6 shows a flow chart of one embodiment of a method of determining the TOF of an acoustic signal.

FIG. 6 shows a flow chart of one embodiment of an algorithm 600 of determining the time-of-flight of an acoustic signal.

In a first step 610, a drive electrical signal is provided to a transmit acoustic transducer in a transmit device. As discussed above, in some embodiments the drive electrical signal may be modulated to provide a timing marker therein.

In a step 620, in response to the drive electrical signal, a transmit acoustic transducer transmits an acoustic signal.

Coincident with transmitting the acoustic signal, the transmit acoustic transducer also transmits an electromagnetic wave.

In a step 630, a receive acoustic transducer of a receive device receives the electromagnetic wave that is emitted by the transmit acoustic transducer coincident with transmitting the acoustic signal.

In a step 640, the receive device detects a first feature of the received electromagnetic wave, and determines a first time $t_{REF}$ corresponding to the first feature. Any of the various techniques discussed above may be employed to determine the In a step 650, the receive acoustic transducer receives the acoustic signal.

In a step 660, the receive device detects a second feature of the received acoustic signal and determines a second time $t_{REC}$ corresponding to the second feature.

In a step 670, the receive device determines a difference between the second time $t_{REC}$ and the first time $t_{REF}$.

In a step 680, the time-of-flight $t_{TOF}$ of the acoustic signal is estimated as the difference between the second time $t_{REC}$ and the first time $t_{REF}$.

While example embodiments are disclosed herein, one of ordinary skill in the art appreciates that many variations that are in accordance with the present teachings are possible that remain within the scope of the appended claims. The embodiments therefore are not to be restricted except within the scope of the appended claims.

The invention claimed is:

1. A method, comprising:
   providing a drive electrical signal to a piezoelectric bulk or microelectromechanical system (MEMS) transmit acoustic transducer in a transmit device;
   in response to the drive electrical signal, coincidently transmitting both an electromagnetic wave and an acoustic signal from the piezoelectric bulk or MEMS transmit acoustic transducer;
   receiving the electromagnetic wave at a receive acoustic transducer of a piezoelectric bulk or MEMS receive device;
   demodulating the received electromagnetic wave;
   detecting a first feature of the received and demodulated electromagnetic wave and determining a first time corresponding to the first feature, wherein the first feature corresponds to at least one of a peak amplitude and a marker placed in the electromagnetic wave by the piezoelectric bulk or MEMS transmit acoustic transducer;
   receiving the acoustic signal at the piezoelectric bulk or MEMS receive acoustic transducer of the receive device;
   demodulating the received acoustic signal;
   detecting a second feature of the received and demodulated acoustic signal and determining a second time corresponding to the second feature, wherein the second feature corresponds to at least one of a peak amplitude and a marker placed in the acoustic signal by the piezoelectric bulk or MEMS transmit acoustic transducer;
   determining a difference between the second time and the first time; and
   estimating the time-of-flight of the acoustic signal as the difference between the second time and the first time.

2. The method of claim 1, further comprising providing electromagnetic shielding between the piezoelectric bulk or MEMS transmit acoustic transducer and the piezoelectric bulk or MEMS receive acoustic transducer, wherein the electromagnetic shielding attenuates a magnitude of the electromagnetic wave received by the receive device.

3. The method of claim 1, wherein the acoustic signal is a pulsed acoustic signal having a pulse duration that is less than the time-of-flight of the acoustic signal.

4. The method of claim 1, wherein the first feature is the peak amplitude of the electromagnetic wave, and the second feature is the peak amplitude of the acoustic signal.

5. The method of claim 1, wherein the first feature is the marker placed in the received electromagnetic wave by at least one of amplitude, phase or frequency modulation of the drive electrical signal, and the second feature is a corresponding marker placed in the received acoustic signal.

6. The method of claim 1, wherein detecting the first feature and determining the first time comprises performing a first correlation between the received electromagnetic wave and a first correlation reference and detecting a time corresponding to a correlation peak in the first correlation, and wherein detecting the second feature and determining the second time comprises performing a second correlation between the received acoustic signal and a second correlation reference and detecting a time corresponding to a correlation peak in the second correlation.

7. The method of claim 6, wherein the first and second correlation references each comprise a copy of the drive electrical signal.

8. The method of claim 6, wherein the first and second correlation references each comprise a signal received by the piezoelectric bulk or MEMS receive acoustic transducer.

9. The method of claim 1, wherein the first feature and the second feature are placed in the electromagnetic wave and acoustic signal, respectively, by a modulation technique employed by the piezoelectric bulk or MEMS transmit acoustic transducer.

10. The method of claim 9, wherein the modulation technique comprises Frequency-Shift Keying (FSK) modulation.

11. The method of claim 9, wherein the modulation technique comprises Phase-Shift Keying (PSK) modulation.

12. The method of claim 9, wherein the modulation technique comprises Quadrature Modulation.

13. The method of claim 9, wherein the modulation technique comprises Frequency Hopping.

14. An apparatus, comprising:
   a receive device comprising a piezoelectric bulk or microelectromechanical system (MEMS) receive acoustic transducer; and
   a processor configured to cause the receive device to execute an algorithm comprising:
      receiving at the piezoelectric bulk or MEMS receive acoustic transducer an electromagnetic wave that is emitted coincidently with transmitting an acoustic signal by a piezoelectric bulk or MEMS transmit acoustic transducer;
      detecting a first feature of the received electromagnetic wave and determining a first time corresponding to the first feature, wherein the first feature corresponds to at least one of a peak amplitude and a marker placed in the electromagnetic wave by the piezoelectric bulk or MEMS transmit acoustic transducer;
      receiving the acoustic signal at the piezoelectric bulk or MEMS receive acoustic transducer;
      detecting a second feature of the received acoustic signal and determining a second time corresponding to the second feature, wherein the second feature corresponds to at least one of a peak amplitude and a marker placed in the acoustic signal by the piezoelectric bulk or MEMS transmit acoustic transducer;

determining a difference between the second time and the first time; and estimating the time-of-flight of the acoustic signal as the difference between the second time and the first time.

15. The apparatus of claim 14, further comprising a transmit device including the piezoelectric bulk or MEMS transmit acoustic transducer that is separated and spaced apart from the piezoelectric bulk or MEMS receive acoustic transducer.

16. The apparatus of claim 15, further comprising electromagnetic shielding between the transmit device and the receive device that attenuates a magnitude of the electromagnetic wave received by the receive device.

17. The apparatus of claim 14, further comprising at least one correlator adapted to correlate the received electromagnetic wave and a first correlation reference, and to correlate the received acoustic signal and a second correlation reference.

18. The apparatus of claim 17, wherein the first and second correlation references each comprise a copy of a drive electrical signal provided to drive the piezoelectric bulk or MEMS transmit acoustic transducer.

19. The apparatus of claim 17, wherein the first and second correlation references each comprise a signal received by the piezoelectric bulk or MEMS receive acoustic transducer.

20. The apparatus of claim 14, wherein the processor is further configured to cause the receive device to demodulate the received electromagnetic wave and the received acoustic signal to identify the marker in the received electromagnetic wave and the received acoustic signal.

* * * * *